US00PP17296P2

(12) United States Plant Patent
Hansen

(10) Patent No.: US PP17,296 P2
(45) Date of Patent: Dec. 19, 2006

(54) ***HOSTA* PLANT NAMED 'HOLLYWOOD LIGHTS'**

(50) Latin Name: *Hosta hybrida*
Varietal Denomination: Hollywood Lights

(75) Inventor: Hans Andrew Hansen, Waseca, MN (US)

(73) Assignee: Shady Oaks Nursery, LLC, Waseca, MN (US)

( * ) Notice: Subject to any disclaimer, the term of this patent is extended or adjusted under 35 U.S.C. 154(b) by 5 days.

(21) Appl. No.: 11/244,646

(22) Filed: Oct. 6, 2005

(51) Int. Cl.
*A01H 5/00* (2006.01)

(52) U.S. Cl. ..... Plt./353
(58) Field of Classification Search ..... Plt./353
See application file for complete search history.

*Primary Examiner*—Wendy Haas
(74) *Attorney, Agent, or Firm*—Penny J. Aguirre

(57) ABSTRACT

A new cultivar of *Hosta* named 'Hollywood Lights', a sport of *Hosta* 'On Stage', that is characterized by its unique variegated foliage with wide dark green margins comprising up to two thirds of the leaf area and centers that emerge yellow and change to yellow-green in summer. 'Hollywood Lights' is a large sized *Hosta* with a mounded plant habit and very pale lavender flowers that emerge in mid summer.

2 Drawing Sheets

Botanical classification: *Hosta hybrida.*
Cultivar designation: 'Hollywood Lights'.

BACKGROUND OF THE INVENTION

The present invention, *Hosta* 'Hollywood Lights', relates to a new and distinct cultivar of *Hosta,* botanically known as a *Hosta hybrida,* hereinafter referred to as 'Hollywood Lights'.

The inventor selected the new cultivar, 'Hollywood Lights', in a garden in Waseca, Minn. 'Hollywood Lights' originated in 1998 as a chemically induced sport of *Hosta* 'On Stage' (unpatented). 'Hollywood Lights' is unique from 'On Stage' in having foliage with a significantly wider dark green edge.

Asexual reproduction of the new cultivar was first accomplished by the inventor by division in Waseca, Minn. in 2004. Asexual reproduction of the new cultivar by division and tissue culture has shown that the unique features of 'Hollywood Lights' are stable and reproduced true to type in successive generations.

SUMMARY OF THE INVENTION

The following traits have been repeatedly observed in trials in Minnesota for a period of six years and represent the characteristics of the new cultivar. These attributes in combination distinguish 'Hollywood Lights' as a new and unique cultivar of *Hosta.*

1. The foliage of 'Hollywood Lights' is variegated with wide dark green margins and centers that emerge yellow and mature to yellow-green, the margin width comprises up to two thirds of the leaf area. The leaf margin of 'Hollywood Lights' is significantly wider than the parent plant, 'On Stage'.
2. 'Hollywood Lights' is a large sized *Hosta* with a mounded plant habit, reaching a height of about 58 cm (exclusive of flower scapes) and a spread of about 1 mm in six years.
3. 'Hollywood Lights' blooms in mid summer with very pale lavender flowers.

BRIEF DESCRIPTION OF THE DRAWING

The accompanying colored photographs illustrate the overall appearance and distinct characteristics of the new *Hosta.* The photographs in the figures were taken of mature plants of 'Hollywood Lights' and 'On Stage' as grown outdoors in Waseca, Minn. under similar conditions for six years.

Figure 1:
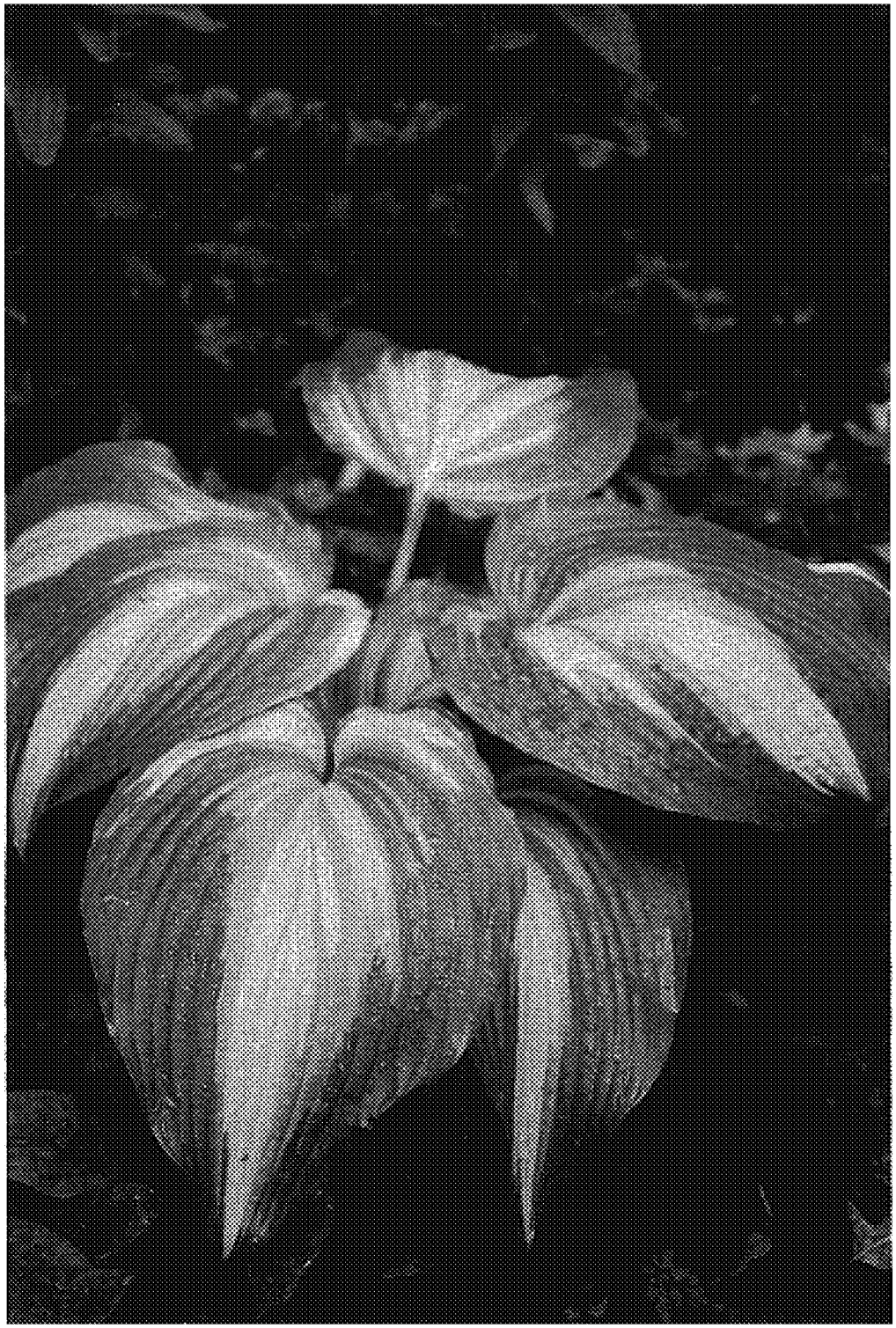
FIG. 1 provides an overall view of the plant habit and the foliage of the new cultivar, 'Hollywood Lights', as observed in spring.
Figure 2:
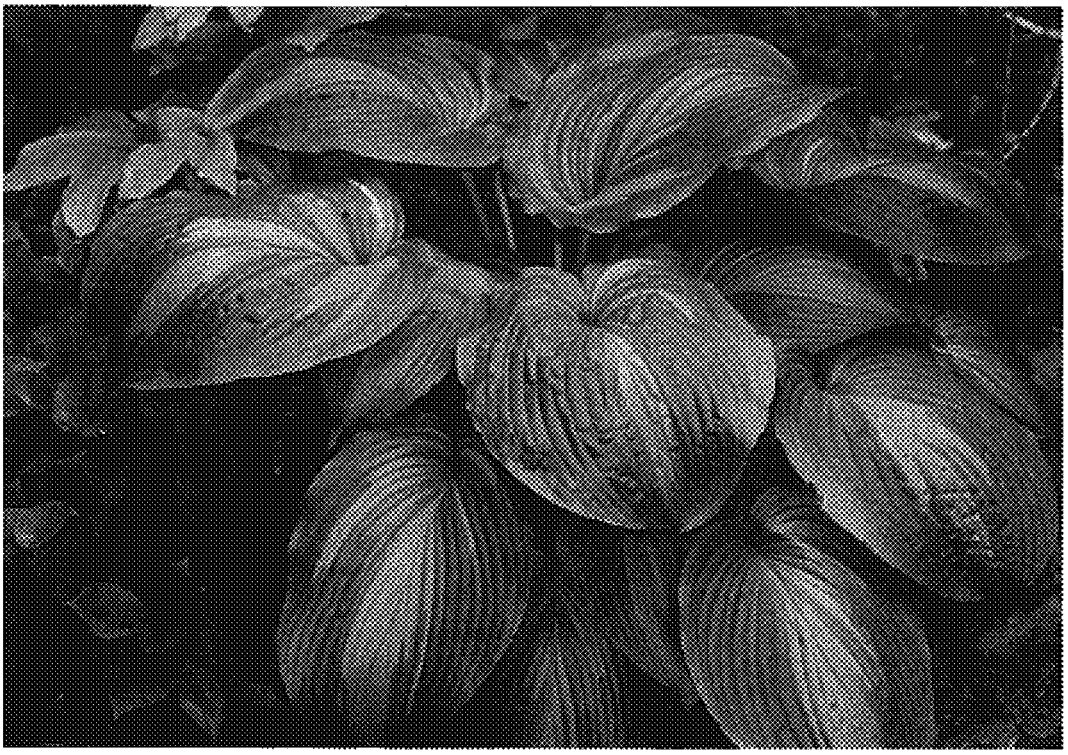
FIG. 2 provides an overall view of the plant habit and the foliage of 'Hollywood Lights' as observed in summer.
Figure 3:
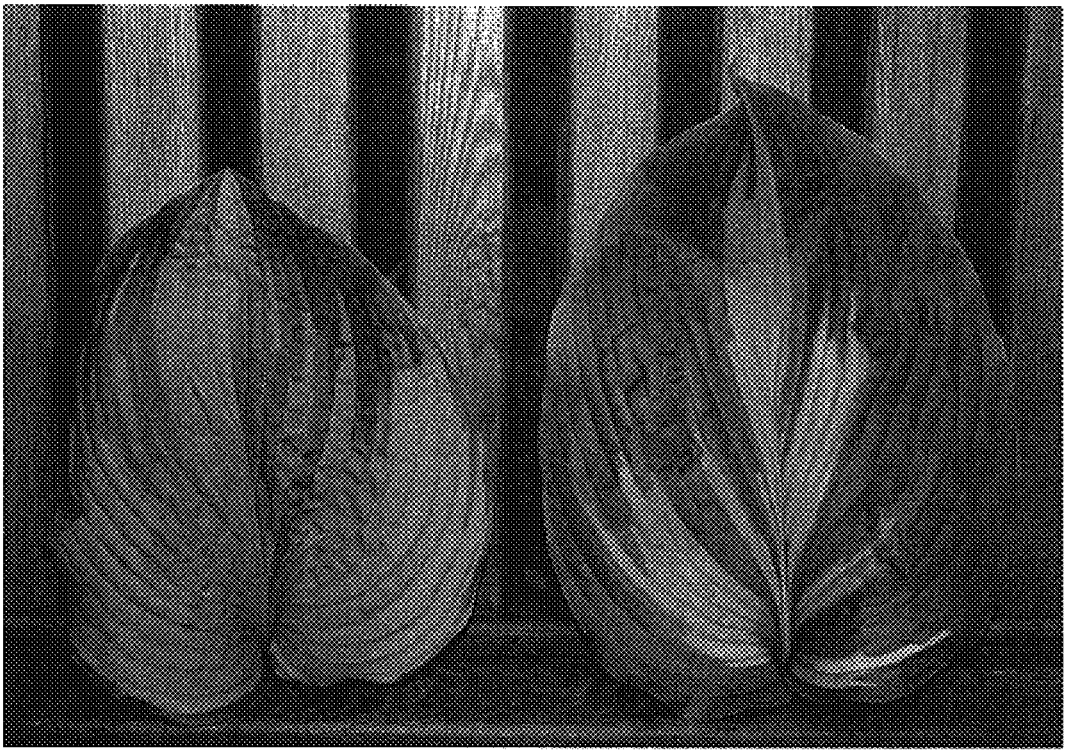
FIG. 3 provides a comparison between a leaf of 'Hollywood Lights' (shown on right) and 'On Stage' (shown on left).

The colors in the photographs are as close as possible with the photographic and printing technology utilized and combined with the color values cited in the detailed botanical description accurately describe the colors of the new *Hosta.*

DETAILED BOTANICAL DESCRIPTION OF THE PLANT

The following is a detailed description of six year-old plants of the new cultivar as grown outdoors in Waseca, Minn. The phenotype of the new cultivar may vary with variations in environmental, climatic, and cultural conditions, as it has not been tested under all possible environmental conditions. The color determination is in accordance with the 2001 R.H.S. Colour Chart of The Royal Horticultural Society, London, England, except where general color terms of ordinary dictionary significance are used.

Botanical classification: 'Hollywood Lights' is a cultivar of *Hosta hybrida.*
Parentage: Sport of *Hosta* 'On Stage'.
General description:
*Blooming period.*—About 3 weeks, typically from July 1 to July 28 in Minnesota.

*Plant habit.*—Herbaceous perennial, clump-forming, mounded habit, large leaves.

*Height and spread.*—Reaches about 58 cm (23 in) in height and about 1 m (43 in) in width.

*Hardiness.*—U.S.D.A. Zones 3 to 8.

*Culture.*—Light to full shade, moist soils of moderate fertility.

*Diseases and pests.*—No susceptibility or resistance to diseases or other pests has been observed for 'Hollywood Lights'.

*Root description.*—Freely branched, fleshy.

*Propagation.*—In vitro propagation is the preferred method utilizing typical methods for *Hosta,* division are also possible.

*Root development.*—Rooted transplants from tissue culture fully develop in a 96-cell liner in about 6 to 8 weeks in a greenhouse with average temperatures of about 70° F.

*Growth rate.*—Moderate.

Foliage description:

*Leaf shape.*—Broadly ovate.

*Leaf division.*—Simple.

*Leaf base.*—Cordate.

*Leaf apex.*—Cuspidate.

*Leaf aspect.*—Flat to gently pendant.

*Leaf venation.*—About 15 to 16 pairs of veins, campylodrome pattern, impressed on upper surface and raised on lower surface, color matches foliage coloration on upper surface, lower surface 144D.

*Leaf margins.*—Entire, slightly wavy near base.

*Leaf attachment.*—Petiolate.

*Leaf arrangement.*—Basal, radiate spirally from base.

*Leaf surface.*—Glabrous on upper lower surface, shiny on lower surface.

*Leaf substance.*—Average.

*Leaf variegation pattern.*—Dark green margins, bright chartreuse centers with some intermediate coloration between margin and centers on the upper surface of the mature foliage, centers have a elliptical pattern with secondary streaks radiating from base, centers are a brighter in spring.

*Leaf color.*—Spring foliage upper surface; margins 137B, centers 150C. Spring foliage lower surface; margins 138A, centers color between 145C and 138B. Summer foliage upper surface: margins 137A, centers 144B to 144C, intermediate areas of 137D and 144A. Summer foliage lower surface; margins 138A, centers 144A.

*Leaf size.*—Average of 36 cm in length, average of 24 cm in width.

*Leaf quantity.*—About 5 to 7 per shoot (eye).

*Petiole size.*—About 40 cm in length, average 1.5 cm in width.

*Petiole color.*—Inner surface; variegated with margins Inner surface with centers 144C with stripes of 144B, outer surface; narrow margin of 137A, centers 145C with shades of 145B.

*Petiole surface.*—Glaucous, both surfaces.

*Petiole shape.*—Sulcate.

Flower scape description:

*Scape shape.*—Round, solid.

*Scape number.*—One per mature eye under normal growing conditions.

*Scape posture.*—Arching.

*Scape size.*—About 66 cm in length, average of 5 mm in width.

*Scape color.*—144B.

*Scape surface.*—Glabrous.

*Leaf bracts.*—About 2 to 3, about 13 cm in length and 4 cm in width, lanceolate in shape, 137A in color.

Flower description:

*Inflorescence type.*—Terminal racemes of single tubular-shaped flowers.

*Lastingness of inflorescence.*—About 3 weeks from first opening bloom to fading of last opening bloom, individual blooms last about one day.

*Flower shape.*—Tubular.

*Flower number.*—About 35.

*Flower fragrance.*—None.

*Flower bud shape.*—Spathulate.

*Flower bud size.*—Up to about 4 cm in length and 3.5 cm in diameter.

*Flower bud color.*—91D.

*Flower size.*—About 4.5 cm in length and 4.5 cm in diameter.

*Flower color.*—91D.

*Pedicels.*—About 7 mm in length and 2 mm in diameter, 144B in color.

*Perianth features.*—Comprised of 6 tepals, 3 interior and 3 exterior, fused in tube region and about one half of expanded region then overlapping towards apex.

*Tepal shape.*—Spatulate.

*Tepal size.*—About 4.5 cm in length, up to 1.3 cm in width.

*Tepal color.*—91D.

*Tepal texture.*—Glabrous.

*Floral bracts.*—1 per flower, lanceolate in shape, papery, 137A in color, about 1.5 cm in length and 3.5 cm in width.

Reproductive organs:

*Gynoecium.*—1 Pistil. Style is about 5.5 cm in length, 1 mm in width and 155B in color. Stigma is 3-lobed, 155B in color and 0.75 mm in diameter. Ovary is superior, compound, composed of 3 locules, oblong in shape, 5 mm in length, 2 mm in width and 144D in color.

*Androecium.*—6 stamens, filament is 155B in color, about 5 cm in length, 0.7 mm in width, anthers are 3 mm in length, 1.5 mm in width, attachment is versatile, 202A in color, dehiscence is longitudinal, pollen is abundant and 15C in color.

*Fruit.*—Capsule, 3-chambered, about 2.5 cm in length, 7 mm in width, 138A to 138B in color.

*Seeds.*—About 20 seeds per capsule, about 8 mm in length and 3 mm in width, 202A in color.

I claim:

1. A new and distinct cultivar of *Hosta* plant named 'Hollywood Lights' as herein illustrated and described.

* * * * *